(12) United States Patent
Lessard et al.

(10) Patent No.: US 7,713,260 B2
(45) Date of Patent: May 11, 2010

(54) CATHETER HAVING AN OVERMOLDED HUB

(75) Inventors: David R. Lessard, Bloomington, IN (US); Scott E. Eells, Bloomington, IN (US); Gregory A. Frankland, Unionville, IN (US); David A. Drewes, Jr., Bloomington, IN (US)

(73) Assignees: Cook Incorporated, Bloomington, IN (US); Sabin Corporation, Bloomington, IN (US)

( * ) Notice: Subject to any disclaimer, the term of this patent is extended or adjusted under 35 U.S.C. 154(b) by 1177 days.

(21) Appl. No.: 10/937,862

(22) Filed: Sep. 9, 2004

(65) Prior Publication Data

US 2005/0059958 A1 Mar. 17, 2005

Related U.S. Application Data

(60) Provisional application No. 60/501,991, filed on Sep. 11, 2003.

(51) Int. Cl.
*A61M 39/10* (2006.01)
(52) U.S. Cl. .................. 604/533; 604/523
(58) Field of Classification Search .......... 604/523, 604/533
See application file for complete search history.

(56) References Cited

U.S. PATENT DOCUMENTS

| | | | | |
|---|---|---|---|---|
| 3,721,231 A * | 3/1973 | Hubert | .......... | 600/435 |
| 4,670,009 A | 6/1987 | Bullock et al. | .......... | 604/533 |
| 5,797,869 A * | 8/1998 | Martin et al. | .......... | 604/43 |
| 5,830,401 A | 11/1998 | Prichard et al. | .......... | 264/262 |
| 6,056,721 A | 5/2000 | Shulze | .......... | 604/102 |
| 6,146,354 A | 11/2000 | Beil et al. | .......... | 605/28 |
| 6,245,053 B1 | 6/2001 | Benjamin | .......... | 604/523 |
| 6,575,959 B1 * | 6/2003 | Sarge et al. | .......... | 604/533 |

FOREIGN PATENT DOCUMENTS

| | | |
|---|---|---|
| EP | 0 495 263 A | 7/1992 |
| WO | WO 9922800 A2 * | 5/1999 |

OTHER PUBLICATIONS

International Search Report from corresponding PCT Application No. PCT/US2004/029484 dated May 9, 2005, 3 pages.
PEBAX® RESINS 33 Series Property Comparison (1p), BC:5/94, Technical Information.

(Continued)

*Primary Examiner*—Nicholas D Lucchesi
*Assistant Examiner*—Laura A Bouchelle
(74) *Attorney, Agent, or Firm*—Brinks Hofer Gilson & Lione

(57) ABSTRACT

Catheters having an overmolded hub are disclosed. The overmolded catheter hubs may include one or more access hubs that are overmolded with an overmold material. The catheter hub may also be formed as a single piece from the overmold material. The overmolded construction can result in a stronger bond between the catheter body and the hub and can provide for access hubs having sufficient clarity for the observation of air bubbles in a contained fluid. The disclosed catheter hubs may also demonstrate improved balloon deflation rates when utilized with a catheter body having a distal balloon.

28 Claims, 4 Drawing Sheets

OTHER PUBLICATIONS

Grilamid TR 55, Grilamid® EMS, (2p), Jun. 26, 2000. Product Data Bulletin. (EMS-CHEMIE (North America) Inc., 2060 Corporate Way, Sumter, SC, www.emschem.com, welcome@us.emschem.com).

Properties Table of Injection Molding Grades—Technical Data, (1p).

Vestamid, 2 Comparative Tables of Grades, Technical Information (1p).

Standard Test Method for Haze and Luminous Transmittance of Transparent Plastics, *ASTM International*, 100 Barr Harbor Drive, West Conshohocken, PA, (6p), Aug. 29, 2003.

Pebax Antistatic Additive—Technical Information, *Elf Atochem (ATO)*, (11p).

Vestamid Polyamide 12 Elastomers—Technical Information, (23p).

* cited by examiner

CATHETER HAVING AN OVERMOLDED HUB

This application claims priority under 35 U.S.C. §119(e) to provisional application No. 60/501,991 by David R. Lessard, et al. and entitled Catheter Having an Overmolded Hub, filed Sep. 11, 2003, which is hereby incorporated by reference herein.

BACKGROUND

Catheters are tube-like medical instruments that may be inserted into a body cavity, organ, or blood vessel for diagnostic or therapeutic reasons. Catheters may be designed for insertion into the vasculature and are available for a wide variety of purposes, including diagnosis, interventional therapy, drug delivery, drainage, perfusion, and the like. They may also be useful for other procedures, such as gynecological procedures, cardiac procedures, general interventional radiology procedures, and the like. Catheters for each of these and other purposes can be introduced to numerous target sites within a patient's body by guiding the catheter through an incision made in the patient's skin and a blood vessel and then through the body to the target site.

Catheters generally have an elongated, flexible catheter body with a catheter side wall enclosing one or more catheter lumens. The lumens can extend from a catheter body proximal end, where the catheter body is coupled to a relatively more rigid catheter hub, to a distal end. The one or more lumens may have the same diameter throughout the length of the catheter or taper, such as when the lumens have a larger diameter at the proximal end than at the distal end. The catheter hub typically has one or more access hubs that provide for the insertion of wires or the attachment of syringes or other devices, for example. The catheter body may be relatively straight, inherently curved, or curved by insertion of a curved stiffening wire or guide wire through a catheter lumen. The catheter body may assume a straight or linear configuration, when free from external bending forces. The catheter body may be highly flexible, thus able to pass through the tortuous twists and turns of a patient's vasculature. In some cases, the catheter body may have a shaped distal end portion including curves and bends which are selected to facilitate introduction and placement of the catheter in the vascular system. A particular geometry of curves and/or bends may be selected to accommodate the intended use of the catheter. The distal end of the catheter may also be equipped with an inflatable balloon to expand a medical device, such as a stent, and/or to dilate a vessel.

The body and side wall of the catheter may be fabricated and dimensioned to minimize the outer diameter of the catheter body and the thickness of the side wall. In this fashion, the diameter of the catheter lumen may be maximized while retaining sufficient side wall flexibility and strength characteristics to enable the catheter to be used for the intended medical purpose.

The catheter body may have a length in the range from about 40 cm to 200 cm, usually having a length in the range from about 60 cm to 175 cm. The diameter of the catheter body may be in the range of about 0.67 mm (2 F) to about 7 mm (21 F). The catheter body may define one or more inner lumens that may have inside diameters ranging from about 0.4 mm to about 6 mm.

The body and/or side wall of the catheter may be made from any suitable material, including, but not limited to, polyethers and polyester block amides. For example, the side wall may be made from a polyether block amide, which may include a copolymer of amide monomers copolymerized with polyether monomers. Because the amide monomers may have greater structural "rigidity" in comparison to the polyether monomers, the rigidity of the resulting catheter body to deformation, such as bending or stretching, may be controlled. One example of a suitable polyether block amide from which the catheter body and/or side wall may be made is PEBAX®, which is available from Elf Atofina, Philadelphia, Pa. In one aspect, a blend of PEBAX® polyether block amides may be used.

The catheter body may be constructed with one or more additional elongated, flexible bodies or tubes residing within the outermost body. Thus, the outermost tube may contain one or more inner tubes defining additional inner lumens. In this fashion, a first lumen may be formed in the interior of an inner tube, while a second lumen may be formed between an outer wall of an inner tube and the inner wall of the outermost tube. When an inner tube is placed substantially in the center of the outermost tube, the lumens may be coaxially arranged as shown in FIG. 3C.

The catheter may also be constructed with one or more longitudinal partitions that contact the outermost wall at two or more locations and reside within the outermost body. In this fashion, a first lumen may be formed between a first side of a partition and the outermost wall, while a second lumen may be formed between a second side of the partition and the outermost wall. In this arrangement, the lumens have separate centers. A catheter body having an internal arrangement of this type is depicted in FIG. 1A.

The inner tube or tubes that form the lumens may be made from a single material, such as a lubricious polymer, or a combination of materials. Lubricious polymers include, but are not limited to, fluorocarbons, such as polytetrafluoroethylene (PTFE), polyamides, such as nylons, polyether block amides (PEBA), polyolefins, polyimides, and the like. The inner tube may also be a laminate structure comprising a non-lubricious outer layer and an inner lumen surrounding layer or coating of a more lubricious material. When one or more lumens are formed by one or more partitions, the partitions may be formed from the same material as the outermost wall; however, this is not required.

The end of the catheter that remains external to the body cavity (proximal end) terminates in a catheter hub. A conventional catheter hub 14, such as that depicted in the catheter 100 of FIG. 1, is a single piece that is directly bonded to the catheter body 12 with an adhesive at one or more adhesive bonds 18. The conventional catheter hub 14 may include one or more access hubs, such as a first lumen access hub 15 and a second lumen access hub 16. The lumen access hubs provide ingress and egress from the mouths 17 of the access hubs to one or more lumens, such as the first lumen 26 and the second lumen 28, respectively. The lumens may have a substantially smaller diameter than the access hubs. The access hubs 15 and 16 may be female luer type connectors or another type of connector. A skive 20 is a passageway through a catheter side wall 13 of the catheter 100 and may provide fluid communication between the second lumen access hub 16 and the second lumen 28.

Fluids, gases, wires, and the like may be passed from the mouths of the access hubs, through the lumens, and optionally into the body cavity. For example, a stiffening or directing wire may be threaded through the first lumen access hub 15 and into the first lumen 26. This wire may then be utilized to guide the catheter through the body cavity. A fluid, such as a viscous liquid, pharmaceutical preparation, or gas, may be directed through the second lumen access hub 16, the skive 20, and into the second lumen 28. If the catheter 100 is a balloon type catheter, this fluid may inflate a balloon at the distal end of the catheter that is in fluid communication with the second lumen 28.

While the conventional catheter 100 can be effective, disadvantages exist for the conventional catheter hub 14. These disadvantages are in the areas of construction and performance. Regarding construction, when the hub 14 is assembled, the portion of the first lumen access hub 15 that tapers in diameter 30 to meet the first lumen 26 must be aligned with the first lumen 26. Because the first lumen 26 may have a relatively small diameter, on the order of a few millimeters or less, alignment can be difficult. It may also be difficult to form the first lumen junction 13, where the access hub 15 and the lumen 26 are bonded by adhesive or other means. It is also necessary to adhesively bond the catheter body 12 with the catheter hub 14, ensuring that the skive 20 aligns with the second lumen access hub 16. Such meticulous construction can be difficult and time consuming. Due to the small surface areas to which the adhesive may be applied, separation of the catheter body from the hub is also possible.

The conventional catheter hub 14 may also have performance disadvantages resulting from the entrapment areas 32 that reside between the second lumen access hub 16 and the catheter side wall 13 and at the proximal end of the second lumen 28. When a fluid is introduced into the second lumen access hub 16, especially if it is a viscous fluid, the fluid not only passes through the skive 20, but also exerts considerable pressure on the adhesive bonds 18 that hold the catheter side wall 13 to the catheter hub 14 in the area of skive 20. This flow is depicted as the second lumen flow 24. If too great, this pressure can lead to failure of the adhesive bonds 18 and result in separation of the catheter body 12 from the catheter hub 14. Thus, if a balloon is inflated at the distal end of the catheter with fluid introduced through the second lumen access hub 16, a limitation may be placed on the pressure to which the balloon may be inflated and the rate at which the fluid may be introduced to the balloon. This can lead to lengthy inflation times. Additionally, because there is little mechanical support in the area of the skive 20, the fluid may crush the side wall to some extent, thus reducing fluid flow into the second lumen 28.

Similarly, because fluid must pass from the second lumen 28, through the skive 20, and through the entrapment areas 32 before exiting through the second lumen access hub 16, a limitation is placed on how quickly the balloon may deflate. The entrapment areas 32 can disrupt and/or create turbulence in the fluid flow out of the catheter, thus significantly impeding deflation of the balloon.

SUMMARY

A catheter is provided that has an overmolded hub construction. The overmold may be formed from a hardened thermoplastic or resin that couples the hub to a catheter body. The overmold hub may include one or more access hubs and one or more anchoring features that the thermoplastic or resin may fill prior to hardening. Fluid communication may be established between the one or more catheter lumens and the one or more access hubs by extending a catheter tube into a lumen access hub, through the use of a removable insert, through the use of a hollow insert that remains within the overmold hub, and the like.

Other systems, methods, features and advantages of the invention will be, or will become, apparent to one with skill in the art upon examination of the following figures and detailed description. It is intended that all such additional systems, methods, features, and advantages are included within this description, are within the scope of the invention, and are protected by the following claims.

DETAILED DESCRIPTION

Figure 2:
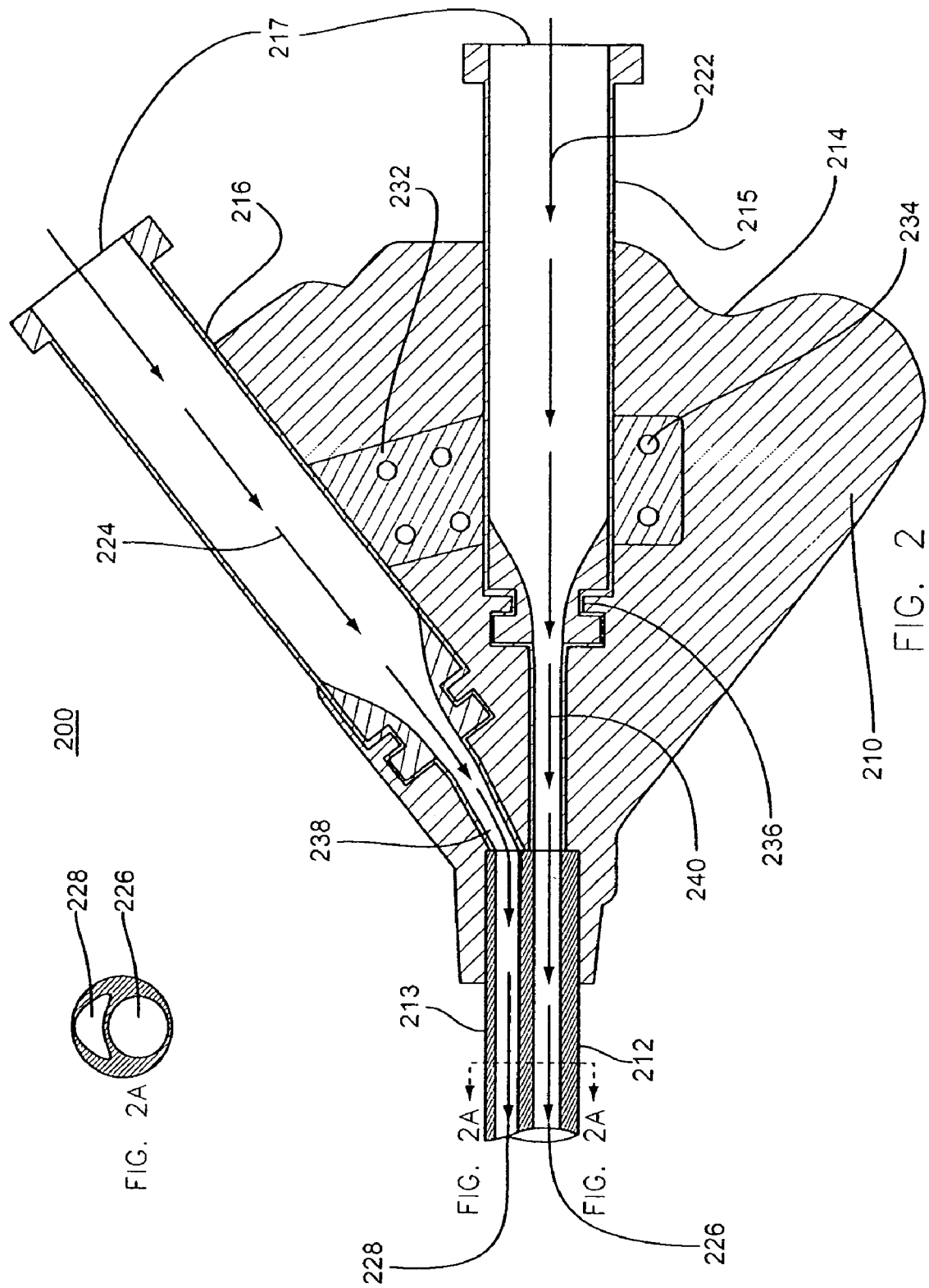
FIG. 2 shows a catheter embodying features of the current invention having proximal entry to the second lumen.

FIG. 2 depicts a catheter 200 having an overmolded catheter hub 214. The overmold catheter hub 214 may be coupled to a catheter body 212 with an overmold material 210. The catheter body 212 has a side wall 213 and may have a plurality of lumens, such as a first lumen 226 and a second lumen 228. A first lumen access hub 215 and a second lumen access hub 216 may be coupled by a bridging structure 232. The bridging structure 232 can maintain the desired spatial orientation between the access hubs 215 and 216 and may be a portion of the same piece that includes the access hubs. The overmold hub 214, including any access hubs and any bridging structure or structures, may be molded as a single piece or as multiple pieces. The catheter 200 may have other configurations including those with fewer or additional components.

Figure 1:
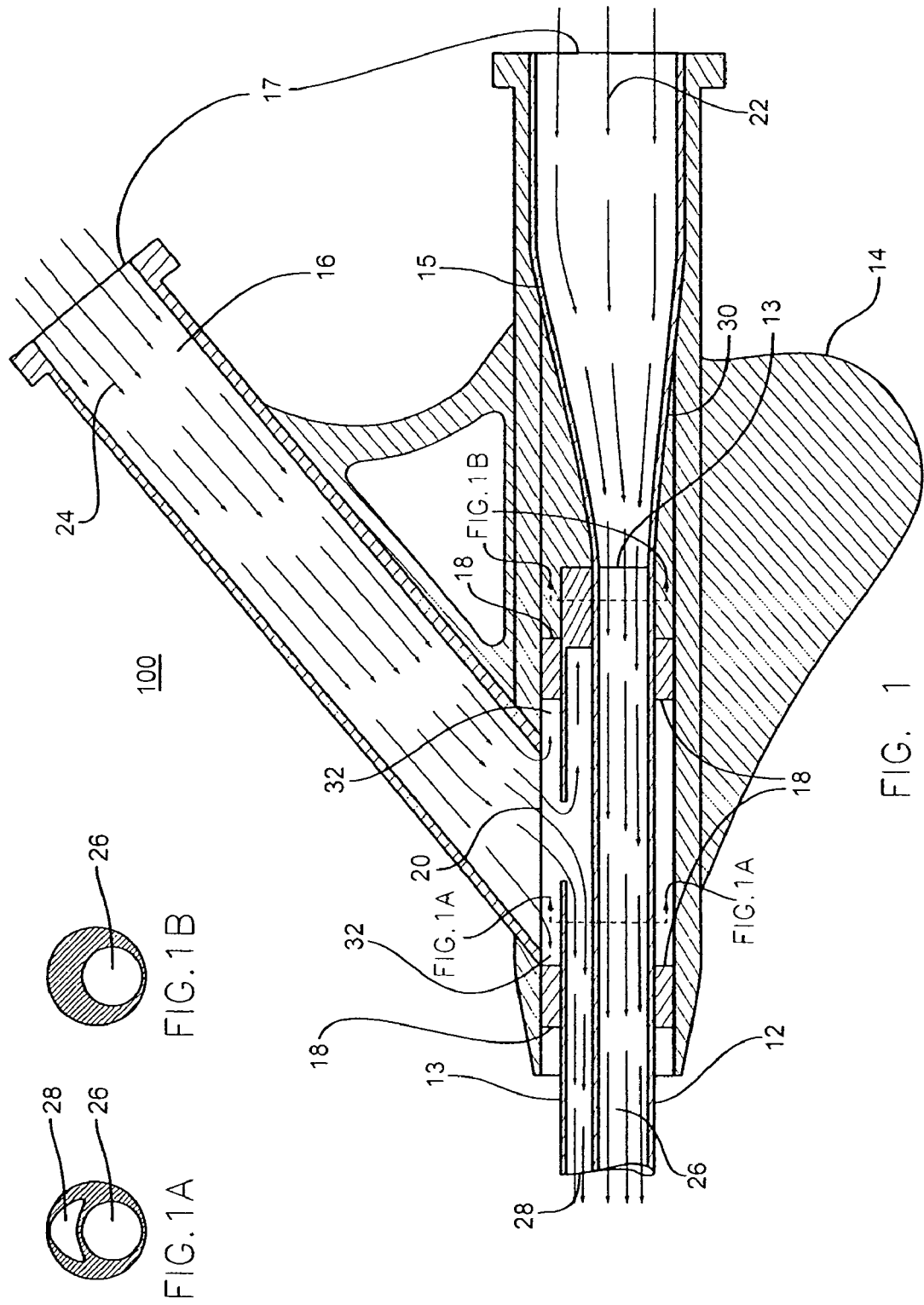
FIG. 1 shows a conventional catheter.

Unlike the conventional catheter hub 14 depicted in FIG. 1, the overmold hub 214 is not bonded to the catheter body with adhesive. Instead, the bridging structure and the access hubs may be separated from the catheter body 212, but held in place by the overmold material 210. The overmold hub 214 may contain one or more anchoring features.

While anchoring features may take any form, they function to assist in holding the overmold hub 214 in position relative to the catheter body 212 after the overmold material hardens. Thus, they may be in the form of the anchoring holes 234 present in the bridging structure 232. In this aspect, the overmold material can pass through the anchoring holes and then harden. Anchoring features may also be in the form of an anchoring groove 236 present in the lumen access hubs 216 and 217, where the overmold material 210 can enter the groove and then harden. Similarly, the bridging structure 232 can function as an anchoring feature. Anchoring features may also be in the form of protruding flanges, grooves, recesses, indentations, protuberances, and the like in any portion of the overmold hub, including the access hubs or the bridging structure.

The access hubs may be made from a plastic that allows the user to see air bubbles that may exist in a contained fluid. Thus, one or more of the access hubs may have clarity sufficient for air bubbles to be observed. This clarity can provide a significant benefit because the user can monitor fluid introduction, such as during the inflation of a balloon, for undesirable air bubbles. Plastics having a suitable clarity for use in the access hubs may have a luminous transmittance of at least about 60%. Suitable plastics also may have a transmittance of at least about 70%. In one aspect, the plastic from which the access hubs can be made has a luminous transmittance of at least about 80%. In another aspect the plastic may have a transmittance of about 85%. Luminous transmittance (the ratio of the luminous flux transmitted by a body to the flux incident upon it) may be measured according to ASTM D1003-00.

In one aspect, the access hubs may be formed from an amorphous polymer, which provides the desired clarity. One suitable amorphous polymer includes an amorphous amide, such as Nylon 12, which has been chemically modified to have an amorphous structure. An example of a modified Nylon 12 is GRILAMID® grade TR-55 and is available from EMS, Sumter, S.C.

The overmold material 210 that surrounds the catheter body 212 may include a thermoplastic that is heated until it reaches a flowable state and that when applied to the catheter body, the access hubs, and any bridging structure, couples these components together and seals any gaps to form the overmolded catheter 200. The thermoplastic may be any polymeric composition that can flow when heated, harden when cooled, and bond with the catheter body 212. Thus, when melted and deposited in a mold, the thermoplastic can be formed into the overmold hub 214. Force may be applied to keep the flowable thermoplastic in the mold. When the thermoplastic hardens, it will retain the shape of the mold, although some shrinkage may occur. Suitable thermoplastics include, but are not limited to amides, such as Nylons, polyurethanes, polycarbonates, polyesters, polyvinylchlorides, polyolefins, styrenics, or combinations thereof. An example of a suitable Nylon is VESTAMID® grade L1670 available from DeGussa, 45764 MARL, Germany.

The overmold material 210 may include a curable resin that is applied to the catheter body as an uncured resin in a semi-solid, liquid, or powdered state. The uncured resin may then be cured with light, heat, radiation, radio frequency, air, a chemical accelerator, or other process that results in a hardening of the resin. Any curable resin that can bond the catheter body 212 to any access hubs and any bridging structure while sealing any gaps may be utilized.

Because the overmold hub 214 is not directly attached with an adhesive to the catheter body 212, other means are utilized to establish fluid communication between the lumens 226 and 228 and the access hubs 215 and 216, respectively. One method to establish the desired fluid communication is to extend a lumen tube, such as a first lumen tube 240, into a lumen access hub, such as the first lumen access hub 215, prior to hardening the overmold material. When the overmold material hardens, the lumen tube is held in the lumen access hub and any gaps may be sealed.

Figure 3:
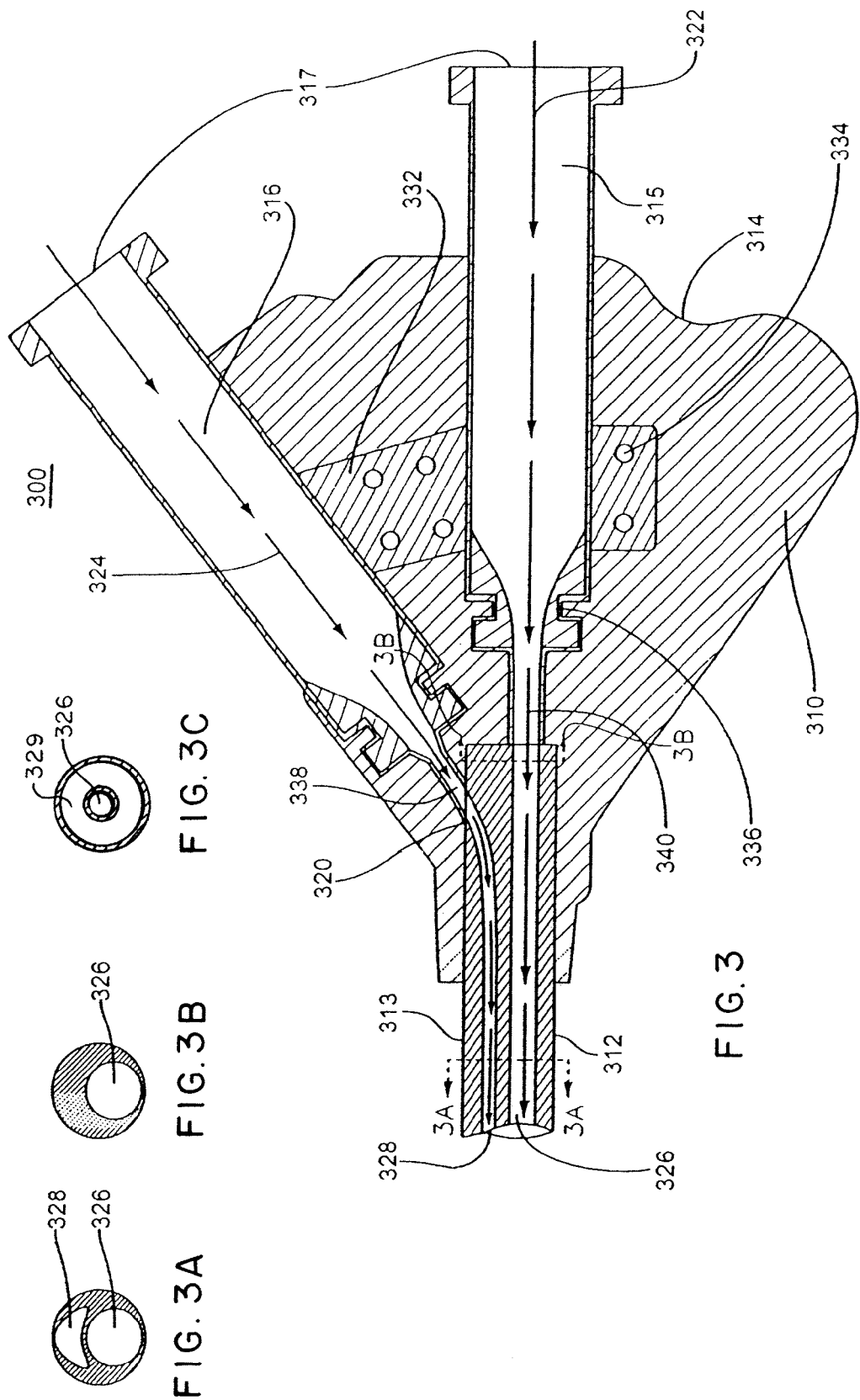
FIG. 3 shows a catheter embodying features of the current invention having skive entry to the second lumen.

Another method of establishing fluid communication between the catheter lumens and the lumen access hubs is to place an insert extending from the interior of a lumen access hub, such as the second lumen access hub 216, into the interior of a lumen in the catheter body, such as into the second lumen 228, prior to adding the overmold material. While FIG. 2 depicts entry into the proximal end of the second lumen 228, entry may be at any convenient location, such as through a skive 320 as shown in FIG. 3 and discussed further below. The insert may be solid or hollow and may be made from plastic, metal, and the like. Thus, when the thermoplastic or the resin hardens, the insert may be removed to leave a passage in the overmold material 210, such as the overmold passageway 238.

If the insert is to be removed after hardening of the overmold material, the insert may be made or coated with a material that does not appreciably couple with the selected overmold material. Such materials may include stainless steel or fluorinated polymers, such as Teflon®. If the insert is hollow, such as if a cannula or the like is used, it may be left in place to establish the desired fluid communication. Additional methods, such as drilling passageways 238 in the overmold material 210 and the like may also be utilized to establish fluid communication between the catheter lumens and the lumen access hubs.

The overmold material can seal any gaps that would otherwise exist, including any openings in the proximal end of the lumens. In this fashion, fluid communication may be established between a catheter lumen and a luer access hub. Other methods of establishing fluid communication between the lumens of the catheter body and the overmold hub 214 may also be used.

The catheter 200 can be simpler to assemble than the conventional catheter 100 as depicted in FIG. 1, at least because the catheter 200 does not require the alignment and bonding of a lumen junction. During assembly, problems may arise with the lap or butt joint used at the lumen junction 13 of the conventional catheter 100, especially where the first lumen tube of the catheter shaft is bonded to the catheter hub. The bonding method used to form the joint can have adverse effects on the concentricity, stiffness, and kink resistance of the catheter body 12. Additionally, the overmold hub 214 of the catheter 200 may be more securely held to the catheter body 212 because a greater surface area exists about the catheter body for the overmold material 210 to bond with during hardening. Because the overmolded construction of catheter 200 does not require a skive, any alignment problems that may arise between the skive and its corresponding lumen access hub may be eliminated.

The design of the catheter 200 also may eliminate the entrapment areas 32 shown in FIG. 1. This may be accomplished by providing a passageway 238 through the overmold material 210 that establishes fluid communication between the lumen access hub 216 and the second lumen 228. The design of the catheter 200 also allows for the introduction of a viscous fluid through the second lumen access hub 216 without the exertion of a compressive force on any adhesive bonds, such as the adhesive bonds 18 as shown in FIG. 1. This may be seen by comparing the second lumen flow 24 in FIG. 1 with the second lumen flow 224 in FIG. 2. Thus, the possibility of separating the catheter side wall 213 from the overmold hub 214 may be reduced for the catheter 200, even if higher pressures are utilized during fluid introduction.

Because the diameter of the overmold passageway 238 may be varied depending on the diameter of the insert, the access into the second lumen 228 may have a larger diameter than when a skive is utilized to access the interior of the lumen. In this manner, the passageway 238 may provide for increased ingress and egress of fluid, even with lower introduction pressures and vacuum, respectively. Thus, if the catheter 200 is equipped with a distal balloon, the balloon may be more rapidly inflated and deflated, while the incidence of device failure may be reduced.

The catheter 200 may be assembled by placing the catheter body 212, the access hubs 215 and 216, and any bridging structure or structures 232 in a mold. One or more lumen tubes, such as the first lumen tube 240, then may be extended into one or more access hubs, such as the first lumen access hub 215. An insert then may be placed through one or more access hubs, such as the second lumen access hub 216, and into the catheter body, such as into the second lumen 228. The overmold material then may be added to the mold.

By using a mold that is patterned with the desired features of the access hubs, such as a female luer, the overmold hub 214 may be formed as a single piece. In this aspect, one or more lumen tubes, such as the first lumen tube 240, may be extended into the portion of the mold that will form one or more access hubs, such as the first lumen access hub 215. One or more inserts then may be placed through the portion of the mold that will form the one or more access hubs, such as the second lumen access hub 216, and into the catheter body, such as into the second lumen 228. The overmold material then may be added to the mold.

One method of adding the overmold material is by injecting a hot thermoplastic or resin into an insertion mold containing the components of the catheter. The overmold material then may be hardened under conditions favorable to the overmold material, the material or materials from which the access hubs and any bridging structure is made, and the catheter body including the catheter side wall 213 and any inner tubes. The one or more inserts may then be removed or left in place if hollow.

FIG. 3 depicts a catheter 300 having an overmolded catheter hub 314. The overmold catheter hub 314 may be attached to a catheter body 312 with an overmold material 310. The catheter body 312 has a side wall 313 and may have a plurality of lumens, such as a first lumen 326 and a second lumen 328. A first lumen access hub 315 and a second lumen access hub 316 may be coupled by a bridging structure 332. The bridging structure 332 can maintain the desired spatial orientation between the access hubs 315 and 316 and may be a portion of the same piece that includes the access hubs. The overmold hub 314, including any access hubs and bridging structure, may be injection molded as a single piece or as multiple pieces, as previously described regarding FIG. 2. The catheter 300 may have other configurations including those with fewer or additional components.

As previously discussed regarding FIG. 2, the overmold hub 314 may contain one or more anchoring features. Suitable thermoplastics and resins for use in the overmold material 310 are discussed in greater detail with regard to FIG. 2 above. The access hubs, including the first access hub 315 and the second access hub 316, also may be made from a plastic that allows the user to see air bubbles that may exist in a contained fluid, as described more fully with regard to FIG. 2.

As was previously discussed for FIG. 2, flow communication between the catheter body 312 and the overmold hub 314 may be established by extending a lumen tube, such as a first lumen tube 340, into a lumen access hub, such as the first lumen access hub 315, prior to hardening the overmold material.

Another method of establishing fluid communication between the catheter lumens and the lumen access hubs is to place an insert extending from the interior of a lumen access hub, such as the second lumen access hub 316, through the skive 320, and into the interior of a lumen in catheter body 312, such as into the second lumen 328. The insert may be inserted prior to adding the overmold material. The insert may be as described above regarding FIG. 2.

Unlike in FIG. 2, to form the catheter 300 of FIG. 3, the insert may be passed through the skive 320 in the catheter side wall 313. After the overmold material hardens, the insert may be removed to leave a passageway 338 through the overmold material 310 that enters at the skive 320. If the insert is hollow, it may be left in place. As shown in FIG. 3B, the overmold material can enter the proximal end of the second lumen 328, thus closing the portion of the second lumen behind the insert. In this fashion, fluid communication may be established between the second lumen access hub 316 and the second lumen 328, with the overmold material sealing any gaps that would otherwise exist, including any open portion of second lumen 328. In this way, the second lumen access hub 316 may also communicate with a second lumen 329 that is coaxial with the first lumen 326 as shown in FIG. 3C. As previously discussed in regard to FIG. 2, other methods of establishing fluid communication between the catheter body 312 and the overmold hub 314, such as cannulas and the like, may also be used.

The catheter 300 may be assembled similarly to the catheter 200 as previously described. In one aspect, catheter 300 is assembled using insert molding. Wire inserts may be placed into the lumens in the catheter body 312 through the access hubs, with the wire that passes through the second lumen access hub 316 entering the second lumen 328 through the skive 320. This assembly, including the catheter body, the inserts, the access hubs, and any desired bridging structure is then placed into a mold cavity. The mold is clamped shut and the overmold material is added to the mold cavity. When the overmold material includes a thermoplastic, the hot thermoplastic is rapidly introduced into the mold cavity to envelop the catheter body, the inserts, the hubs, and any desired bridging structure. Cooling is then introduced to the mold to harden the thermoplastic. The mold is opened and the catheter 300 is ejected. The inserts may then be removed, leaving the catheter body with the overmold hub 314.

While the catheter 300 of FIG. 3 utilizes skive access, it lacks the adhesive bonds 18 and the entrapment areas 32 as shown in the catheter 100 of FIG. 1. This may be seen by comparing the second lumen flow 24 in FIG. 1 with the second lumen flow 324 in FIG. 3. The catheter 300 of FIG. 3, like the catheter 200 of FIG. 2, can provide for the introduction of viscous fluid to the second lumen without the exertion of a compressive force against any adhesive bonds. Thus, the possibility of separating the catheter side wall 313 from the overmold hub 314 may be reduced for the catheter 300 when compared with the catheter 100 of FIG. 1, even if higher pressures are utilized during fluid introduction. Elimination of the entrapment areas from the catheter 300 can result from the skive, which was initially a sharp-edged port, being smoothed by the overmold material to give the smooth overmold passageway 338.

When the overmold material contacts the catheter body 312, a coupling can occur between the overmold material and the catheter body 312, which can be made from a material that is compatible with the overmold material. Thus, a coupling can occur between the catheter body and the overmold material that is chemical, thermal, or a combination of chemical and thermal in nature. If a hot thermoplastic is utilized as the overmold material, the heat can also result in some melting or softening of the catheter body 312 and blending with the overmold material. In one aspect, the overmold material is introduced to the catheter body at sufficient temperature to cause the portion of the catheter side wall penetrated by the skin to soften and remodel. Such remodeling can alter the original shape of the ported catheter side wall to conform with the shape of the insert.

The benefits on distal balloon deflation rates provided by a catheter of type 200, which has a smooth flow path lacking the entrapment areas 32 of conventional catheter 100, may be seen from Table I below. The bodies of the compared catheters were about 120 cm in length. Deflation time is the time required to draw 5 cc of fluid from the catheter into a syringe under vacuum. When the deflation times are compared, the catheter of type 200 shows an about 15% increase in deflation rate. Increases in deflation rates may range from about 5% to about 30%, depending on the particular catheter. Improvements from about 10% to about 20% are common.

TABLE 1

| Trial | Catheter 100 Deflation Time in Seconds | Catheter 200 Deflation Time in Seconds |
|---|---|---|
| 1 | 83 | 65 |
| 2 | 64 | 58 |
| 3 | 82 | 67 |
| 4 | 76 | 71 |
| 5 | 77 | 62 |

The benefits regarding deflation rates provided by a catheter of type 300 increases as the length of the catheter body increases. This can be seen from the comparative deflation rates shown below in TABLE II. Deflation time is the time required to draw 4 cc of fluid from the catheter into a syringe under vacuum. The catheter of type 300 shows an approximately 12% increase in deflation rate when compared with a catheter of type 100 for the 40 and 80 cm catheter body lengths. However, for the 120 cm length body, the catheter of type 300 shows about a 17% increase in deflation rate when compared with a catheter of type 100.

TABLE II

| | 40 cm Catheter Body | | 80 cm Catheter Body | | 120 cm Catheter Body | |
|---|---|---|---|---|---|---|
| Trial | Catheter 100 Seconds | Catheter 300 Seconds | Catheter 100 Seconds | Catheter 300 Seconds | Catheter 100 Seconds | Catheter 300 Seconds |
| 1 | 23 | 19 | 38 | 35 | 53 | 54 |
| 2 | 22 | 18 | 43 | 34 | 62 | 48 |
| 3 | 21 | 21 | 36 | 34 | 65 | 48 |

Figure 4:
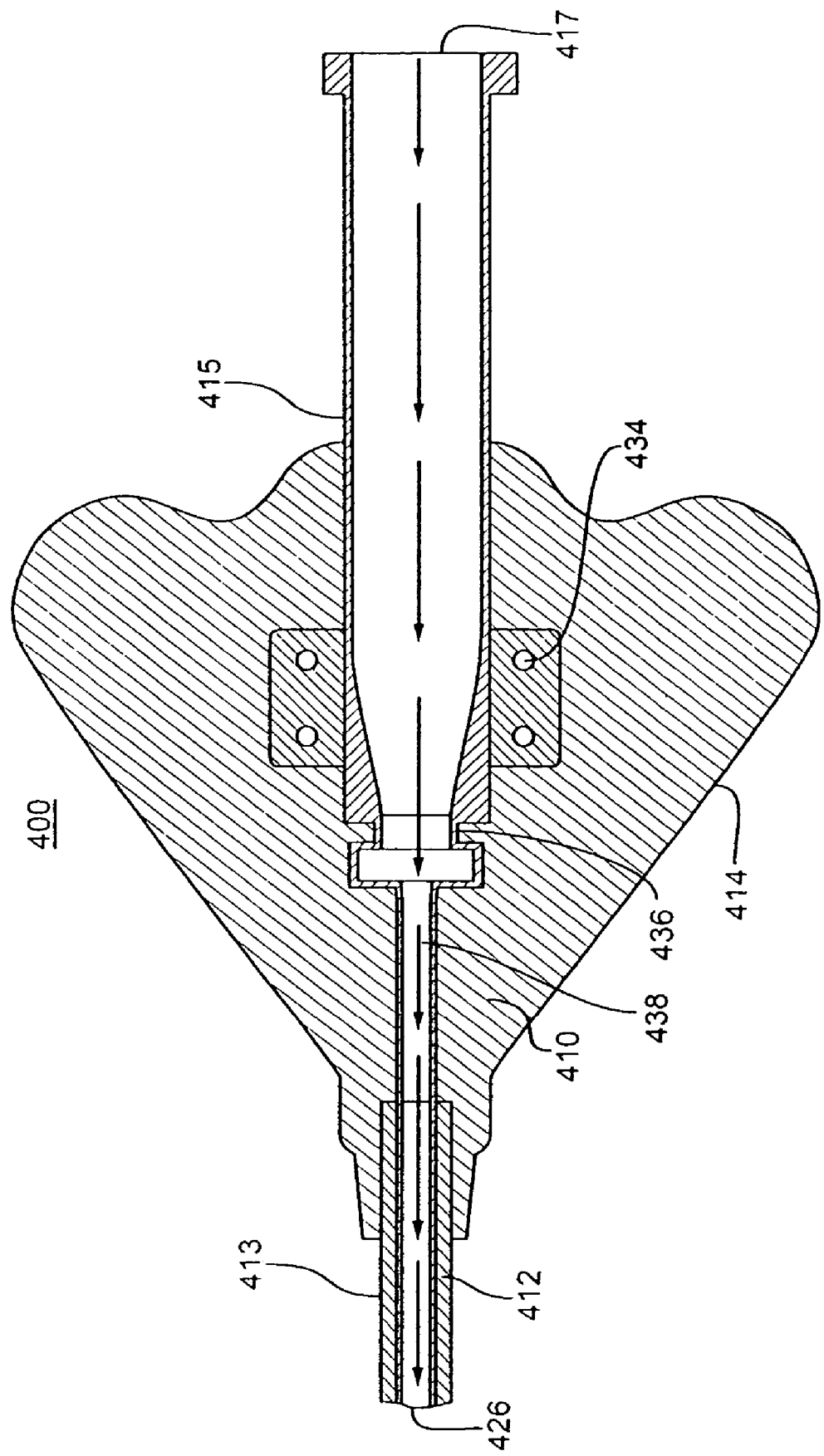
FIG. 4 shows a single lumen catheter embodying features of the current invention.

FIG. 4 depicts a single lumen catheter 400 having an overmolded catheter hub 414. The overmold catheter hub 414 may be attached to a catheter body 412 with an overmold material 410. The catheter body 412 has a side wall 413 and a single lumen 426. A lumen access hub 415 may have anchoring features, including an anchoring hole 434 and an anchoring groove 436. The overmold hub 414, including the access hub, may be injection molded as a single piece or as multiple pieces, as previously described regarding FIG. 2. The catheter 400 may have other configurations including those with fewer or additional components.

As previously discussed regarding FIG. 2, the overmold hub 414 may contain one or more anchoring features. Suitable thermoplastics and resins for use in the overmold material 410 are discussed in greater detail with regard to FIG. 2 above. The lumen access hub 415 may be made from a plastic that allows the user to see air bubbles that may exist in a contained fluid, as described more fully with regard to FIG. 2.

Flow communication between the catheter lumen 426 and the lumen access hub 415 may be established by placing an insert extending from the interior of the lumen access hub 415 into the interior of the catheter lumen 426. The insert may be inserted prior to adding the overmold material. The insert may be as described above regarding FIG. 2. As also previously described, the insert may be removed or left in place if hollow. If the insert is removed, overmold passageway 438 may be formed.

In this fashion, fluid communication may be established between the lumen access hub 415 and the single lumen 426, with the overmold material sealing any gaps that would otherwise exist, including any open proximal portion of the single lumen 426. As previously discussed in regard to FIG. 2, other methods of establishing fluid communication between the catheter body 412 and the overmold hub 414, such as cannulas and the like, may also be used. The catheter 400 may be assembled similarly to the catheters 200 and 300 as previously described.

While various embodiments of the invention have been described, it will be apparent to those of ordinary skill in the art that other embodiments and implementations are possible within the scope of the invention. Accordingly, the invention is not to be restricted except in light of the attached claims and their equivalents.

What is claimed is:

1. A catheter comprising:
   an elongate flexible catheter body having a plurality of lumens including a first lumen and a second lumen, the flexible catheter body having a longitudinal axis extending between a proximal end and a distal end;
   a first access hub and a second access hub, the first access hub being in fluid communication with the first lumen and the second access hub being in fluid communication with the second lumen; and
   an overmold, the overmold overlapping and contacting at least a portion of the catheter body and at least a portion of the first and second access hubs, where the overmold maintains the spatial orientation of the catheter body to the hubs by coupling the catheter body and the hubs.

2. The catheter of claim 1, where the catheter body includes a polyether block amide.

3. The catheter of claim 1, where the lumens are formed from one or more longitudinal partitions.

4. The catheter of claim 1, where the lumens have a substantially coaxial arrangement.

5. The catheter of claim 1, where the lumens are defined by an outermost tube and at least one inner tube.

6. The catheter of claim 1, where the lumens are defined by an outermost tube and a plurality of inner tubes.

7. The catheter of claim 1, where the access hubs include female luer locks.

8. The catheter of claim 1, where the access hubs include an amide.

9. The catheter of claim 8, where the amide includes a nylon chemically modified to have an amorphous structure.

10. The catheter of claim 1, where at least one of the access hubs has a luminous transmittance of at least about 60%.

11. The catheter of claim 8, where at least one of the access hubs has a luminous transmittance of at least about 80%.

12. The catheter of claim 1, further comprising at least one bridging structure, where the at least one bridging structure maintains the spatial orientation of the first access hub to the second access hub.

13. The catheter of claim 12, where the at least one bridging structure includes at least one anchoring feature.

14. The catheter of claim 13, where the at least one anchoring feature is selected from the group consisting of a hole, groove, protruding flange, recess, indentation, and combinations thereof.

15. The catheter of claim 13, where the at least one anchoring feature includes a hole through the at least one bridging structure.

16. The catheter of claim 13, where the at least one anchoring feature includes a groove in the surface of one or more of the access hubs.

17. The catheter of claim 13, where the anchoring feature is at least partially filled by the overmold.

18. The catheter of claim 1, where the overmold comprises at least one passageway providing fluid communication between the first lumen and the first access hub.

19. The catheter of claim 18, where the overmold comprises at least one passageway providing fluid communication between the second lumen and the second access hub.

20. The catheter of claim 19, where the passageway providing fluid communication between the second lumen and the second access hub includes a hollow insert.

21. The catheter of claim 1, where the overmold comprises a cured resin.

22. The catheter of claim 21, where the cured resin couples the plurality of lumens to the plurality of access hubs to provide fluid communication.

23. The catheter of claim 1, where the overmold comprises a thermoplastic.

24. The catheter of claim 23, where the thermoplastic couples the plurality of lumens to the plurality of access hubs to provide fluid communication.

25. The catheter of claim 23, where the thermoplastic is selected from the group consisting of amides, polyurethanes, polycarbonates, polyesters, polyvinylchlorides, polyolefins, styrenics, and combinations thereof.

26. The catheter of claim 23, where the thermoplastic includes an amide.

27. A catheter comprising:
   an elongate flexible catheter body having a lumen, the flexible catheter body having a longitudinal axis extending between a proximal end and a distal end;
   a hub having an access hub in fluid communication with the lumen; and
   an overmold, the overmold overlapping and contacting at least a portion of the catheter body and at least a portion of the hub, where the overmold maintains the spatial orientation of the catheter body to the hub by coupling the catheter body and the hub.

28. The catheter of claim 27, where the overmold results from insert molding.

* * * * *

UNITED STATES PATENT AND TRADEMARK OFFICE
CERTIFICATE OF CORRECTION

PATENT NO. : 7,713,260 B2  Page 1 of 1
APPLICATION NO. : 10/937862
DATED : May 11, 2010
INVENTOR(S) : Lessard et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1407 days.

Signed and Sealed this

Ninth Day of November, 2010

David J. Kappos
*Director of the United States Patent and Trademark Office*